US012668740B2

(12) United States Patent
Hecht et al.

(10) Patent No.: US 12,668,740 B2
(45) Date of Patent: Jun. 30, 2026

(54) METHOD FOR PRODUCING SEMICONDUCTOR QUANTUM DOTS

(71) Applicant: The Trustees of Princeton University, Princeton, NJ (US)

(72) Inventors: Michael Hecht, Skillman, NJ (US); Sarangan Chari, Princeton Junction, NJ (US); Leah Spangler, Monmouth Junction, NJ (US)

(73) Assignee: THE TRUSTEES OF PRINCETON UNIVERSITY, Princeton, NJ (US)

( * ) Notice: Subject to any disclaimer, the term of this patent is extended or adjusted under 35 U.S.C. 154(b) by 597 days.

(21) Appl. No.: 18/179,659

(22) Filed: Mar. 7, 2023

(65) Prior Publication Data

US 2023/0332042 A1      Oct. 19, 2023

Related U.S. Application Data

(60) Provisional application No. 63/317,120, filed on Mar. 7, 2022.

(51) Int. Cl.
    *C30B 7/00*          (2006.01)
    *B01J 20/20*         (2006.01)
    (Continued)

(52) U.S. Cl.
    CPC ........... *C09K 11/565* (2013.01); *B01J 20/205* (2013.01); *B01J 31/062* (2013.01); *C01G 11/02* (2013.01);
    (Continued)

(58) Field of Classification Search
    CPC ........... C30B 7/00; C30B 29/48; C30B 29/46; C30B 29/50
    See application file for complete search history.

(56) References Cited

U.S. PATENT DOCUMENTS

| | | |
|---|---|---|
| 9,293,717 B2 | 3/2016 | Berger et al. |
| 2013/0164792 A1* | 6/2013 | Mori .................... C07D 209/20 |
| | | 435/106 |

(Continued)

OTHER PUBLICATIONS

Arndt et al, "Methods in Molecular Biology", vol. 352: Protein Engineering Protocols (Year: 2007).*

(Continued)

*Primary Examiner* — Matthew J Song
(74) *Attorney, Agent, or Firm* — Meagher Emanual Laks Goldberg & Liao, LLP

(57) ABSTRACT

Biomineralization—the synthesis of inorganic materials using proteins—has recently gained interest as a low cost, green route for the production of metal chalcogenide semiconductor nanocrystals. Typical biomineralization approaches rely on proteins or biomolecules identified from organisms which possess a native biomineralization response. Disclosed herein is an alternative biomineralization approach for synthesizing metal chalcogenide nanocrystals which uses an artificially designed de novo protein. De novo proteins are non-natural proteins, allowing for facile modification of the protein through the tuning of amino acids within the sequence. This de novo protein was employed to produce size-controlled populations of semiconductor nanocrystals, with properties consistent with those produced using traditional routes.

16 Claims, 4 Drawing Sheets

Specification includes a Sequence Listing.

(51) Int. Cl.

| | |
|---|---|
| *B01J 31/06* | (2006.01) |
| *C01G 11/02* | (2006.01) |
| *C07K 14/00* | (2006.01) |
| *C09K 11/56* | (2006.01) |
| *C30B 29/46* | (2006.01) |
| *C30B 29/48* | (2006.01) |
| *C30B 29/50* | (2006.01) |
| *B82Y 20/00* | (2011.01) |
| *B82Y 40/00* | (2011.01) |

(52) U.S. Cl.
CPC .............. *C07K 14/001* (2013.01); *C30B 7/00* (2013.01); *C30B 29/46* (2013.01); *C30B 29/48* (2013.01); *C30B 29/50* (2013.01); *B01J 2231/005* (2013.01); *B01J 2531/002* (2013.01); *B82Y 20/00* (2013.01); *B82Y 40/00* (2013.01); *C01P 2004/64* (2013.01); *C01P 2006/60* (2013.01)

(56) References Cited

U.S. PATENT DOCUMENTS

| | | | |
|---|---|---|---|
| 2016/0265001 A1 | 9/2016 | Berger et al. | |
| 2017/0335309 A1* | 11/2017 | Berger | C12N 15/74 |
| 2019/0256553 A1* | 8/2019 | Levin | B01J 19/08 |

OTHER PUBLICATIONS

Kamtekar, Satwick et al., "Protein Design by Binary Patterning of Polar and Nonpolar Amino Acids," Science, vol. 262, pp. 1680-1685, Dec. 10, 1993.

Hecht, Michael H. et al., "De novo proteins from designed combinatorial libraries," Protein Science, vol. 13, pp. 1711-1723, 2004.

Hoegler, Kenric J. and Hecht, Michael H., "A de novo protein confers copper resistance in *Escherichia coli*," Protein Science, vol. 25, pp. 1249-1259, Jan. 8, 2016.

Dunleavy, Robert et al., "Single-enzyme biomineralization of cadmium sulfide nanocrystals with controlled optical properties," PNAS, vol. 113, No. 19, pp. 5275-5280, May 10, 2016.

Sadeghnejad, Abdolhamid et al., "Single enzyme direct biomineralization of ZnS, Zn x Cd 1-x S and Zn x Cd 1-x S—ZnS quantum confined nanocrystals," RSC Advances, vol. 7, No. 61, pp. 38490-38497, 2017.

Yang, Zhou et al., "Single Enzyme Direct Biomineralization of CdSe and CdSe—CdS Core-Shell Quantum Dots," ACS Applied Materials and Interfaces, vol. 9, No. 15, pp. 13430-13439, Mar. 2017.

Spangler, Leah C. et al., "Low Temperature Aqueous Synthesis of Size-Controlled Nanocrystals Through Size Focusing: A Quantum Dot Biomineralization Case Study," Nanoscale, vol. 10, No. 44, pp. 20785-20795, 2018.

Spangler, Leah C. et al., "Enzymatic biomineralization of biocompatible CuInS 2,(CuInZn) S 2 and CuInS 2/ZnS core/shell nanocrystals for bioimaging," Nanoscale, vol. 9, No. 27, pp. 9340-9351, Jun. 2017.

Spangler, Leah C. et al., "Enzymatic synthesis of supported CdS quantum dot/reduced graphene oxide photocatalysts," Green Chemistry, vol. 21, No. 15, pp. 4046-4054, May 2019.

West, Michael W. and Hecht, Michael H., "Binary patterning of polar and nonpolar amino acids in the sequences and structures of native proteins," Protein Science, vol. 4, pp. 2032-2039, Jul. 26, 1995.

Fisher, Michael A. et al., "De Novo Designed Proteins from a Library of Artificial Sequences Function in *Escherichia coli* and Enable Cell Growth," PLoS One, vol. 6, No. 1, p. e15364, Jan. 2011.

Sun, Qingxiang et al., "Structural Basis for the Inhibition Mechanism of Human Cystathionine Gamma-Lyase, an Enzyme Responsible for the Production of H2S," The Journal of Biological Chemistry, vol. 284, No. 5, pp. 3076-3085, Jan. 30, 2009.

Cunningham, Daryl P. and Lundie, Jr., Leon L., "Precipitation of Cadmium by Clostridium Thermoaceticum," Applied and Environmental Biology, vol. 59, No. 1, pp. 7-14, Jan. 1993.

Wang, C.L. et al., "Aerobic Sulfide Production and Cadmium Precipitation by *Escherichia coli* Expressing the Treponema Denticola Cysteine Desulfhydrase Gene," Applied Microbiology and Biotechnology, vol. 56, Nos. 3-4, pp. 425-430, 2001.

Spangler, Leah C. et al., "Biomineralization of PbS and PbS—CdS Core-Shell Nanocrystals and Their Application in Quantum Dot Sensitized Solar Cells," Journal of Materials Chemistry, vol. A4, No. 16, pp. 6107-6115, 2016.

Yang, Jie et al., "Non-Enzymatic Hydrogen Sulfide Production from Cysteine in Blood Is Catalyzed by Iron and Vitamin B6," Communications Biology, vol. 2, No. 1, p. 194, May 21, 2019.

Yang, Zhou et al., "Biomineralized CdS Quantum Dot Nanocrystals: Optimizing Synthesis Conditions and Improving Functional Properties by Surface Modification," Industrial & Engineering Chemistry Research, vol. 55, No. 43, pp. 11235-11244, Oct. 20, 2016.

Wei, Yinan et al., "Stably Folded De Novo Proteins From a Designed Combinatorial Library," Protein Science, vol. 12, pp. 92-102, 2003.

Wei, Yinan et al., "Solution Structure of a De Novo Protein from a Designed Combinatorial Library," PNAS, vol. 100, No. 23, pp. 13270-13273, Nov. 11, 2003.

Bradley, Luke H. et al., "An Intein-Based Genetic Selection Enables Construction of a High-Quality Library of Binary Patterned De Novo Sequences," Protein Engineering, Design & Selection, vol. 18, No. 4, pp. 201-207, Apr. 22, 2005.

Karas, Christina and Hecht, Michael, "A Strategy for Combinatorial Cavity Design in De Novo Proteins," Life, vol. 10, No. 9, Jan. 23, 2020.

Das, Aditi et al., "Binding of Small Molecules to Cavity Forming Mutants of a De Novo Designed Protein," Protein Science, vol. 20, pp. 702-711, Feb. 16, 2011.

Cherny, Izhack et al., "Proteins from an unevolved library of de novo designed sequences bind a range of small molecules," ACS Synthetic Biology, vol. 1, No. 4, pp. 130-138, Apr. 20, 2012.

Patel, Shona C. and Hecht, Michael H., "Directed Evolution of the Peroxidase Activity of a De Novo Designed Protein," Protein Engineering, Design & Selection, vol. 25, No. 9, pp. 445-451, Jun. 3, 2012.

Digianantonio, Katherine M. et al., "A Protein Constructed De Novo Enables Cell Growth by Altering Gene Regulation," PNAS, vol. 113, No. 9, pp. 2400-2405, Mar. 1, 2016.

Digianantonio, Katherine M. et al., "A Non-Natural Protein Rescues Cells Deleted for a Key Enzyme in Central Metabolism," ACS Synthetic Biology, vol. 6, pp. 694-700, Jan. 5, 2017.

Wang, Michael S. et al., "Unevolved De Novo Proteins Have Innate Tendencies to Bind Transition Metals," Life, vol. 9, Jan. 9, 2019.

Mancini, Joshua A. et al., "Design of a Fe4S4 Cluster into the Core of a De Novo 4-Helix Bundle," Biotechnology and Applied Biochemistry, vol. 67, pp. 574-585, Aug. 21, 2020.

Wang, Michael S. et al., "A Completely De Novo ATPase from Combinatorial Protein Design," Journal of The American Chemical Society, vol. 142, No. 36, pp. 15230-15234, Aug. 24, 2020.

Arai, Ryoichi et al., "Domain-Swapped Dimeric Structure of a Stable and Functional De Novo 4-Helix Bundle protein," The Journal of Physical Chemistry B, vol. 116, pp. 6789-6797, Mar. 8, 2012.

Huang, Po-Ssu et al., "The coming of age of de novo protein design," Nature, vol. 537, pp. 320-327, Sep. 15, 2016.

Kuhlman, Brian et al., "Design of a novel globular protein fold with atomic-level accuracy," Science, vol. 302, pp. 1364-1368, Nov. 21, 2003.

Moffet, David A. and Hecht, Michael H., "De novo proteins from combinatorial libraries," Chemical Reviews, vol. 101, pp. 3191-3203, Sep. 6, 2001.

Kaplan, J. and Degrado, W.F., "De novo design of catalytic proteins," Proceedings of the National Academy of Sciences, vol. 101, No. 32, pp. 11566-11570, Aug. 10, 2004.

Korendovych, Ivan V. and Degrado, William F., "De novo protein design, a retrospective," Quarterly Reviews of Biophysics, vol. 53, No. e3, Feb. 11, 2021.

(56) References Cited

OTHER PUBLICATIONS

Singh, Shailendra et al., "Biologically programmed synthesis of core-shell CdSe/ZnS nanocrystals," Chemical Communications, vol. 46, pp. 1473-1475, Jan. 20, 2010.

Flynn, Christine E. et al., "Synthesis and organization of nanoscale II-VI semiconductor materials using evolved peptide specificity and viral capsid assembly," Journal of Materials Chemistry, vol. 13, pp. 2414-2421, Aug. 27, 2003.

Chiku, Taurai et al., "H2S biogenesis by human cystathionine gamma-lyase leads to the novel sulfur metabolites lanthionine and homolanthionine and is responsive to the grade of hyperhomocysteinemia," The Journal of Biological Chemistry, vol. 284, No. 17, pp. 11601-11612, Apr. 24, 2009.

Yang, Zhou et al., "Biomanufacturing of CdS Quantum Dots, " Green Chemistry, vol. 17, No. 7, pp. 3775-3782, May 2015.

Thorson, Megan K. et al., "Identification of Cystathionine β-Synthase Inhibitors Using a Hydrogen Sulfide Selective Probe," Angewandte Chemie International Edition, vol. 52, No. 17, pp. 4641-4644, 2013.

Yu, W. William et al., "Experimental determination of the extinction coefficient of CdTe, CdSe, and CdS nanocrystals," Chemistry of Materials, vol. 15, pp. 2854-2860, Jun. 7, 2003.

Zhou, Rong et al., "Alternative chiral thiols for preparation of chiral CdS quantum dots covered immediately by achiral thiols," Chemical Communications, vol. 47, pp. 6362-6364, Apr. 12, 2011.

Donnelly, Ann E. et al., A De Novo Enzyme Catalyzes a Life-Sustaining Reaction in *E. coli.*, Nature Chemical Biology, vol. 14, pp. 253-255, Mar. 2018.

Tommos, Cecilia et al., "De novo proteins as models of radical enzymes," Biochemistry, vol. 38, pp. 9495-9507, 1999.

Sturzenbaum, S.R. et al., "Biosynthesis of luminescent quantum dots in an earthworm," Nature Nanotechnology, vol. 8, pp. 57-60, Jan. 2013.

Feldheim, Daniel L. and Eaton, Bruce E., "Selection of biomolecules capable of mediating the formation of nanocrystals," ACS Nano, vol. 1, No. 3, pp. 154-159, Oct. 16, 2007.

Liu, Fang et al., "Enzyme mediated synthesis of phytochelatin-capped CdS nanocrystals," Applied Physics Letters, vol. 97, p. 123703, Sep. 22, 2010.

Choi, Jung Kyu et al., "Chirality inversion of CdSe and CdS quantum dots without changing the stereochemistry of the capping ligand," ACS Nano, vol. 10, pp. 3809-3815, 2016.

Moloney, Micheal P. et al., "Chiral highly luminescent CdS quantum dots," Chemical Communications, vol. 38, pp. 3877-3968, Oct. 14, 2007.

Xie, Renguo et al., "Nucleation kinetics vs chemical kinetics in the initial formation of semiconductor nanocrystals," Journal of the American Chemical Society, vol. 131, pp. 15457-15466, Sep. 9, 2009.

Lamer, Victor K. and Dinegar, Robert H., "Theory, production and mechanism of formation of monodispersed hydrosols," Journal of the American Chemical Society, vol. 72, No. 11, pp. 4847-4854, Nov. 17, 1950.

Stipanuk, Martha H. and Ueki, Iori, "Dealing with methionine/homocysteine sulfur: cysteine metabolism to taurine and inorganic sulfur," Journal of Inherited Metabolic Disease, vol. 34, No. 1, pp. 17-32, Feb. 2011.

Hoegl, Annabelle et al., "Mining the cellular inventory of pyridoxal phosphate-dependent enzymes with functionalized cofactor mimics," Nature Chemistry, vol. 10, No. 12, pp. 1234-1245, Dec. 2018.

Bai, Hong-Juan and Zhang, Zhao-Ming, "Microbial synthesis of semiconductor lead sulfide nanoparticles using immobilized Rhodobacter sphaeroides," Materials Letters, vol. 63, pp. 764-766, Jan. 7, 2009.

* cited by examiner

| | |
|---|---|
| —— | 0 hr |
| ········ | 19 hr |
| ------- | 20 hr |
| - - - - | 21 hr |
| -··-··- | 22 hr |
| --- --- | 23 hr |
| ---··--- | 24 hr |

| | |
|---|---|
| ········ | 19 hr |
| -------- | 20 hr |
| - - - - | 21 hr |
| -··-··- | 22 hr |
| --- --- | 23 hr |
| ---··--- | 24 hr |

SEQUENCE LISTING

```
Sequence total quantity: 1
SEQ ID NO: 1              moltype = AA   length = 102
FEATURE                   Location/Qualifiers
source                    1..102
                          mol_type = protein
                          organism = synthetic construct
SEQUENCE: 1
MYGKLNEILE QFDEVLDQLD KNWHKRGNNL HDIEDELHQL VKHFHHFMQG HKNEGKLQDM  60
FDQMQQLLEN FDNHLQKRNE TVHHIHEKLN QLIHQFDHLV HR                     102
```

METHOD FOR PRODUCING SEMICONDUCTOR QUANTUM DOTS

CROSS-REFERENCE TO RELATED APPLICATIONS

This application claims priority to U.S. Provisional Patent Application No. 63/317,120, filed Mar. 7, 2022.

STATEMENT REGARDING FEDERALLY SPONSORED RESEARCH OR DEVELOPMENT

This invention was made with government support under Grant No. MCB-1947720 awarded by the National Science Foundation. The government has certain rights in the invention.

SEQUENCE LISTING

The instant application contains a Sequence Listing which has been submitted electronically in XML file format and is hereby incorporated by reference in its entirety. Said XML copy, created on Jun. 23, 2023, is named Princeton-83403_SL.xml and is 2,056 bytes in size.

TECHNICAL FIELD

The present disclosure is drawn to techniques for producing semiconductor quantum dots, and specifically to using de novo proteins for producing quantum dots.

BACKGROUND

This section is intended to introduce the reader to various aspects of art, which may be related to various aspects of the present invention that are described and/or claimed below. This discussion is believed to be helpful in providing the reader with background information to facilitate a better understanding of the various aspects of the present invention. Accordingly, it should be understood that these statements are to be read in this light, and not as admissions of prior art.

There are numerous applications of quantum dots in a biological context. However, there are few methods for producing bio-compatible quantum dots as most traditional synthesis methods use toxic-precursors which are difficult or impossible to remove.

BRIEF SUMMARY

Various deficiencies in the prior art are addressed below by the disclosed compositions of matter and techniques.

In various aspects, a method for producing a semiconductor nanocrystal may be provided.

The method may include producing and/or purifying the de novo protein prior to introducing the protein into the buffer. The de novo protein may include an amino acid sequence matching a binary pattern of polar (P) and non-polar (N) amino acids, and the de novo protein may be a pyridoxal phosphate (PLP) binding de novo Protein. In some embodiments, the de novo protein may include an amino acid sequence having a sequence having at least 80% sequence identity to MYGKLNEILE QFDEVLDQLD KNWHKRGNNL HDIEDELHQL VKHFHHFMQG HKNEGKLQDM FDQMQQLLEN FDNHLQKRNE TVHHIHEKLN QLIHQFDHLV HR [SEQ ID NO. 1]. In some embodiments, the buffer may include, e.g., N-Methylmorpholine (NMM).

The method may include combining various components in a buffer, including a de novo protein as disclosed herein, a metal salt, a sulfur-containing substrate, and PLP to the buffer. The metal salt may comprise, e.g., Cd. The sulfur-containing substrate may be an amino acid, and may be, e.g., L-cysteine and/or D-cysteine.

The method may include allowing a semiconductor nanocrystal to form. This may include allowing the de novo protein to bind to a PLP cofactor to generate catalytic activity, and using the catalytic activity to produce the semiconductor nanocrystal. The semiconductor nanocrystal may be a metal chalcogenide semiconductor nanocrystal, such as a CdS nanocrystal. In some embodiments, the semiconductor may include a single crystal phase.

The method may include allowing the formed semiconductor nanocrystal to grow to a predetermined size.

The method may include capturing $H_2S$ generated during the formation of the semiconductor nanocrystal, and may include using the captured $H_2S$ to synthesize a different material (such as a reduction of graphene oxide).

In various aspects, a catalyzing agent may be provided. The catalyzing agent may include a de novo protein as disclosed herein, bound to a pyridoxal phosphate (PLP) cofactor.

In various aspects, a system may be provided. The system may include a buffer solution containing a metal salt, a sulfur-containing substrate in the buffer solution, and a de novo protein as disclosed herein in the buffer solution.

BRIEF DESCRIPTION OF DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION

The following description and drawings merely illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be only for illustrative purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or, unless otherwise indicated (e.g., "or else" or "or in the alternative"). Also, the various embodiments described herein are not necessarily mutually exclusive, as some embodiments can be combined with one or more other embodiments to form new embodiments.

The numerous innovative teachings of the present application will be described with particular reference to the presently preferred exemplary embodiments. However, it should be understood that this class of embodiments provides only a few examples of the many advantageous uses of the innovative teachings herein. In general, statements made in the specification of the present application do not necessarily limit any of the various claimed inventions. Moreover, some statements may apply to some inventive features but not to others. Those skilled in the art and informed by the teachings herein will realize that the invention is also applicable to various other technical areas or embodiments.

Rather than identifying a natural catalyst, it has been determined that a de novo protein may be used to catalyze the mineralization of semiconductor quantum dots, such as CdS nanocrystals.

Figure 1:
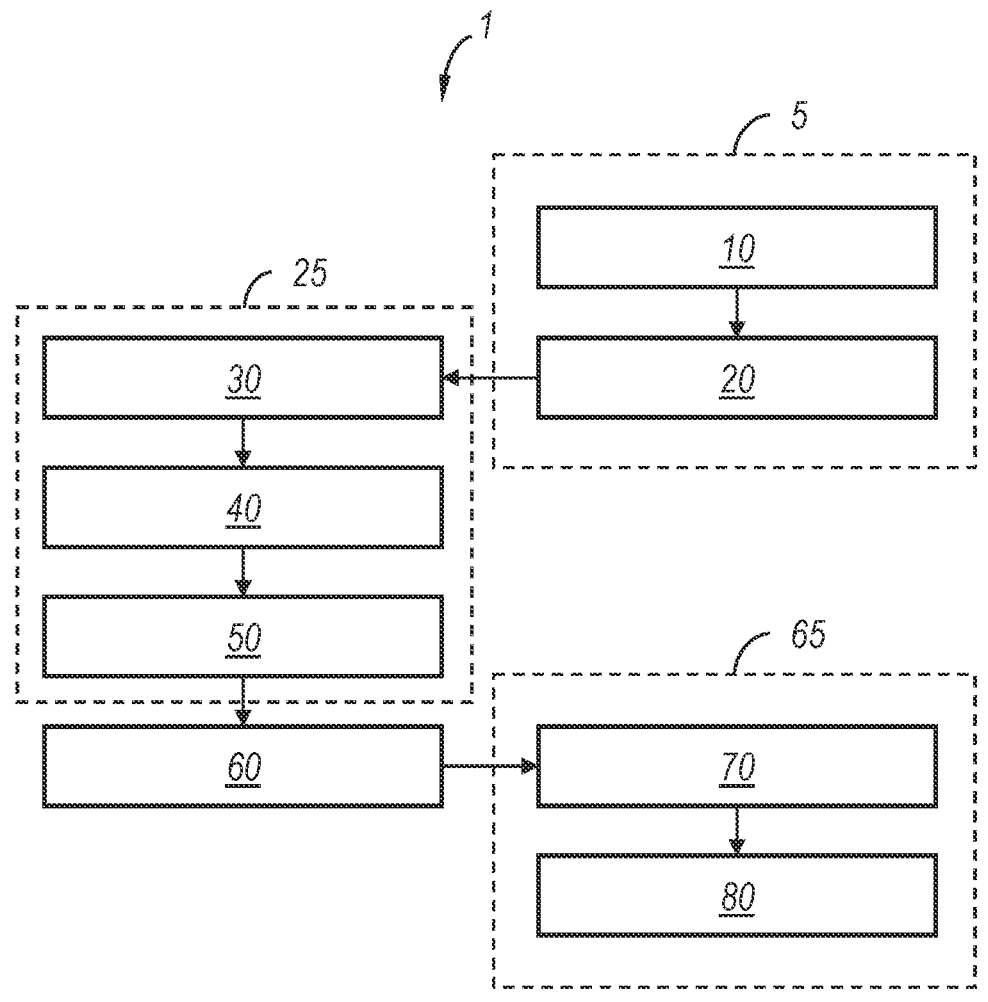
FIG. 1 is a flowchart of an embodiment of a method.

Disclosed herein is a biological method for producing semiconductor quantum dots using de novo proteins. Referring to FIG. 1, the method 1 may some or all of the following steps.

First, the method may include one or more steps related to preparing 5 a de novo protein for use in the quantum dot synthesis. This may include producing 10 the de novo protein. De novo proteins are created in the laboratory from amino acid sequences that share no common ancestry with naturally evolved systems. One class of de novo proteins, pioneered by the Hecht group comprises large combinatorial collections of sequences that are designed using a strategy that relies on a binary code for protein design. Such proteins, including techniques for creating them, are well known. See, e.g., Kamtekar, S., et al., "Protein design by binary patterning of polar and nonpolar amino acids", *Science* 262, 1680-1685 (1993) and Hecht, M. H., et al., "De novo proteins from designed combinatorial libraries", *Protein Sci.* 13, 1711-1723 (2004), the contents of which are each incorporated by reference herein in its entirety. The binary code specifies the pattern of polar and nonpolar amino acids while allowing the exact identities of the individual side chains at each position to vary combinatorially. This approach facilitates the construction of libraries of proteins containing millions of different sequences. In particular, the binary code has produced several libraries of proteins that fold into 4-helix bundle structures. Importantly, these proteins were neither selected by nature nor do they have any relationship to natural biochemical pathways.

The de novo protein should be a PLP Binding de novo Protein. As used herein, the term "PLP Binding de novo Protein" refers to a polypeptide comprising or consisting of four α-helices, wherein each α-helix comprises a binary patterned sequence of seven amino acid residues, or heptad sequence, defined by $[PNPPNNP]_n$, where each "P" is independently selected from the polar amino acid residues Lys (K), His (H), Glu (E), Gln (Q), Asp (D), Asn (N), Thr (T) and Ser (S), each "N" is independently selected from the nonpolar amino acid residues Phe (F), Leu (L), He (I), Met (M), Val (V) and Trp (W), and n is an integer from 2 to 6, and preferably n=3 or 4.

The heptad sequences in an α-helix containing more than one heptad sequence can be identical (i.e., repeats of the same heptad sequence) or they can be different (i.e., each PNPPNNP heptad sequence within the same α-helix can have a different amino acid sequence). Furthermore, the amino acid composition of the α-helices in a PLP Binding de novo Protein can vary from helix to helix such that, for example, each of the α-helices in the protein will have a different amino acid sequence.

A PLP Binding de novo Protein may optionally include additional amino acid residues, for example, N-terminal to the first α-helix and/or C-terminal to the last α-helix in the protein.

A PLP Binding de novo Protein will also include inter-helical turns between the α-helices, wherein each interhelical turn includes one or more amino acid residues (preferably between 2-8 residues, and more preferably 4-6 residues), selected from amino acids that are compatible with the formation of turns. Such amino acids may include, e.g., Gly (G), His (H), Gin (Q), Asn (N), Asp (D), Glu (E) and Lys (K)).

The PLP Binding de novo Protein is generally between 75 amino acid residues and 160 amino acid residues in length (e.g., 102 amino acid residues). In some embodiments, the PLP Binding de novo Protein is between 96 and 102 amino acid resides in length.

In some embodiments, the de novo protein may include an amino acid sequence having a sequence having at least 80%, at least 90%, at least 95%, at least 97%, at least 98%, at least 99%, or 100% sequence identity to the sequence of the ConK protein: MYGKLNEILE QFDEVLDQLD KNWHKRGNNL HDIEDELHQL VKHFHHFMQG HKNEGKLQDM FDQMQQLLEN FDNHLQKRNE TVHHIHEKLN QLIHQFDHLV HR [SEQ ID NO. 1].

The preparation steps may include purifying 20 the protein. This may be done in any appropriate purification technique. For example, in some embodiments, the protein includes an affinity tag, and/or purification may utilize, e.g., affinity chromatography.

Example 1

Expression and Purification of ConK and Mutants

ConK and a mutated protein, K56R, were expressed using recombinant *E. coli* as described previously. See K. J. Hoegler, K. J. and Hecht, M. H., "A de novo protein confers copper resistance in *Escherichia coli*: Novel protein confers copper resistance", *Protein Sci.* 25, 1249-1259 (2016). The plasmid encoding ConK was transformed into BL21 (DE3) *E. coli*. Following transformation, cells were plated onto LB supplemented with chloramphenicol (30 µg/mL) and grown overnight at 37° C. A single colony was then used to inoculate a 2 L volume of LB broth supplemented with 30 μg/mL chloramphenicol. This culture was grown at 37° C. until the cell concentration reached an $OD_{600}$ of about 0.5. At this time, IPTG (final concentration of 100 μM) was added to induce protein expression, followed by incubation at 18° C. overnight. Following overexpression, cells were recovered by centrifugation at 3,000×g and frozen at −20° C. for later use.

Immediately prior to purification, frozen cell pellets containing overexpressed ConK were thawed and resuspended in 25 mL of 50 mM Tris and 300 mM NaCl (buffer A) at 4° C. for 30 min. The resuspended cells were then sonicated on ice using a probe-tip sonicator for a total of 4 min (pulse 10/50 s on/off) and 30% amplitude. Next, the lysate was clarified by centrifugation at 35,000×g for 30 min to separate the soluble overexpressed proteins from cell debris. The protein-rich supernatant was filtered using 0.22-μM PES membrane syringe filters.

The proteins were purified using immobilized metal affinity chromatography (IMAC) followed by size-exclusion chromatography (SEC). While ConK does not carry a canonical histidine tag (6×His) typically required for IMAC, its sequence contains a high percentage of histidine (ca. 14%) enabling nickel binding. First, the filtered supernatant containing ConK was applied to a 5-mL HisTRAP column (GE Healthcare) and equilibrated with five column volumes of running buffer containing 50 mM Tris and 300 mM sodium chloride at pH 7.5. A second wash step using five column volumes of 50 mM imidazole, 50 mM Tris, and 300 mM NaCl at pH 8 removed any nonspecifically bound proteins. ConK was then eluted using 375 mM imidazole, 50 mM Tris, and 300 mM NaCl. The eluates were analyzed by SDS-PAGE, and the appropriate fractions were pooled and further purified by SEC on a HiLoad Superdex 75 26/600 column (GE Healthcare). SEC also removes imidazole from the IMAC stage. This two-stage process typically yields proteins of greater than 95% purity, as assessed by SDS-PAGE. ESI-MS measurements were performed on 10-uL of protein following separation on an HPLC (Agilent 6220 accurate-mass time-of-flight LC/MS). Further characterization of ConK oligomerization was performed using analytical ultracentrifugation (Optima AUC from Beckman Coulter Life Sciences with absorbance and interference detection modules).

The method may include combining 25 various components to a buffer, e.g., to form a solution. This may include adding 30 a de novo protein as disclosed herein to the buffer.

Any appropriate buffer may be utilized. For example, in some embodiments, the buffer may include a buffering agent such as, e.g., N-Methylmorpholine (NMM), a salt (such as NaCl), 4-(2-hydroxyethyl)-1-piperazineethanesulfonic acid (HEPES), and/or tris(hydroxymethyl)aminomethane (Tris). In some embodiments, the buffering agent may be present in a concentration of 100 mM or less. In some embodiments, the buffering agent may be present in a concentration of 50 mM or less. The buffer may be an aqueous buffer. The pH value of the buffer may be adjusted to a pH value of 6 to 8.5.

The method may include adding 40 a metal salt and a sulfur-containing substrate to the solution. The method will generally include the desulfurization of the sulfur-containing substrate, catalyzed by the de novo protein, to form, e.g., $H_2S$, which can then be used to react with the metal salt to form a semiconductor quantum dot.

In some embodiments, the metal salt may be selected from I-VI, II-VI, IV-VI and III-V semiconductor metals. The metal salt may comprise Cd, Ce, Cu, Fe, Hg, In, Ga and/or Zn. In some embodiments, the metal salt may comprise a Cd metal. In some embodiments, the metal salt may be, e.g., $CdCl_2$.

The metal salt may be present in any appropriate amount. In some embodiments, the concentration of the metal salt in the solution is 5 mM or less. In some embodiments, the concentration is 1 mM or less.

The sulfur-containing substrate may be an amino acid, and may be, e.g., L-cysteine and/or D-cysteine.

In some the sulfur-containing substrate may be present in any appropriate amount. In some embodiments, the concentration of the sulfur-containing substrate in the solution is 20 mM or less. In some embodiments, the concentration is 10 mM or less.

The method may include adding 50 pyridoxal phosphate (PLP) cofactor to the buffer. In some embodiments, the PLP may be added at a concentration of 0-200 μM. In some embodiments, the PLP may be added at a concentration of 0-80 μM. The PLP may form a Schiff base, e.g., with a lysine in the de novo protein.

It will be understood that the various addition steps may be performed in any order.

The method may include allowing 60 a semiconductor nanocrystal to form. This may include allowing the de novo protein to bind to a PLP cofactor to generate catalytic activity, and using the catalytic activity to produce the semiconductor nanocrystal.

The resulting semiconductor nanocrystal will depend upon the components in the reaction mixture. If the metal salt comprises Cd, for example, the semiconductor nanocrystal may be a metal chalcogenide semiconductor nanocrystal, such as a CdS nanocrystal.

Example 2

Synthesis of Quantum Dots

Various quantum dot syntheses were initiated by first preparing a solution of 1 mM cadmium chloride (99%, from Sigma-Aldrich) and 10 mM L-cysteine (>97%, from Sigma-Aldrich) in 50 mM NMM at pH 7.5. To this solution, various concentrations (0 to 0.25 mg/mL) of ConK were added, followed by various amounts of PLP (0 to 80 μM), to initiate the biomineralization process. Following addition of PLP, the reaction mixture was placed in a 37° C. incubator with shaking for up to 48 hrs.

The formed semiconductor nanocrystal may be allowed to grow to a predetermined size. This may be done by adjusting the amount of time the reaction mixture is allowed to incubate. A difference in size can be seen via, e.g., a change in the fluorescence of quantum dot solutions over time.

Example 3

Controlling Size of Nanocrystals

As discussed herein, the de novo protein may be used to catalyze the desulfurization of cysteine to $H_2S$, which can be used to synthesize nanocrystals in solution (in this example, synthesizing CdS nanocrystals).

Figure 2A:
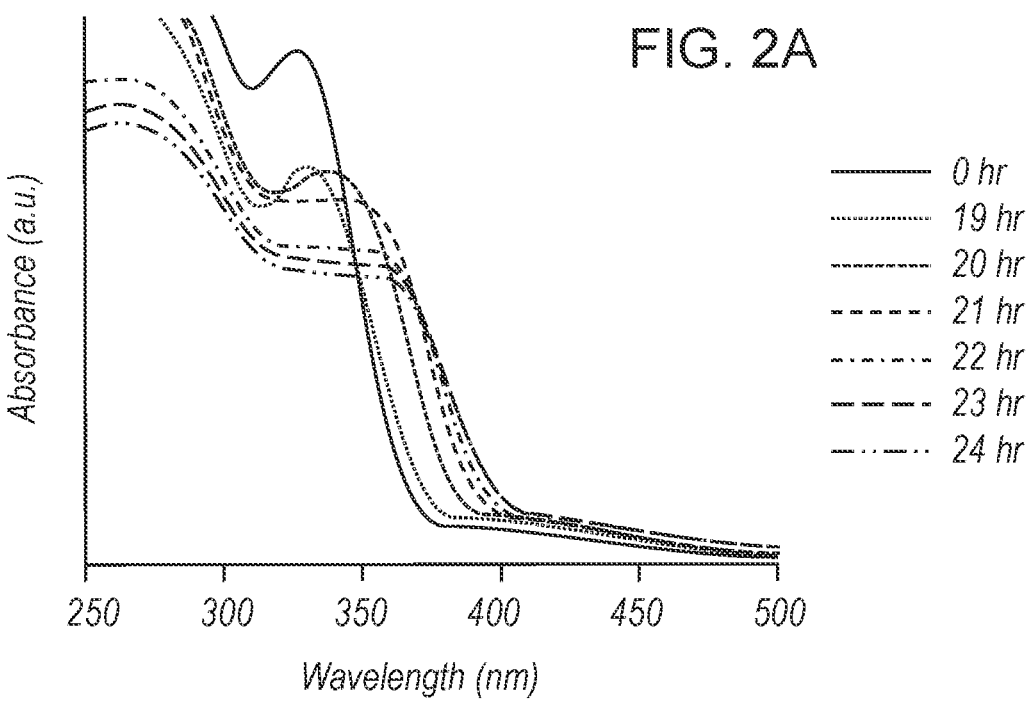
FIGS. 2A and 2B are graphs showing the time course of absorbance (2A) and fluorescence spectra (2B) of CdS nanocrystal solutions grown with 0.25 mg/mL ConK and 32 mM PLP.

A solution containing $CdCl_2$, cysteine, ConK (0.2 mg/mL), and PLP (32 mM) was incubated. Absorbance and fluorescence were monitored for 24 hours. At early times, the only observable peak was at 330 nm from the expected cysteine—PLP complex. However, after incubation for 19 h at 37° C., this peak decreased, with a concomitant increase of a peak at 340 nm, indicating the formation of CdS nanocrystals. See FIG. 2A.

Following their initial appearance, the CdS nanocrystals continued to grow for approximately 8 h, as shown by an absorbance peak that moved to longer wavelengths over time. See FIG. 2A. After 24 h, the peak stabilized at 380 nm, suggesting the nanocrystals grew to a fixed final size. The wavelength of the absorbance can be correlated to the size of the nanocrystals using a size-dependent Beer law calculation. Based on the absorbance maximum, the CdS nanocrystals appear to shift in size from approximately 1.47 to 2.5 nm over the course of 24 h. The fluorescence peak maxima of the CdS nanocrystal populations, shown in FIG. 2B, also shows a shifting wavelength over time. The size distribution of the resulting CdS nanocrystal populations can be evaluated by calculating the full width at half maximum (FWHM) of the fluorescence peak, which indicates population dispersity. The FWHM values, seen in Table 1, below, range from 159 to 177 nm, consistent with relatively broad size distributions commonly observed for CdS nanocrystals synthesized via biomineralization.

TABLE 1

Figure 2B:
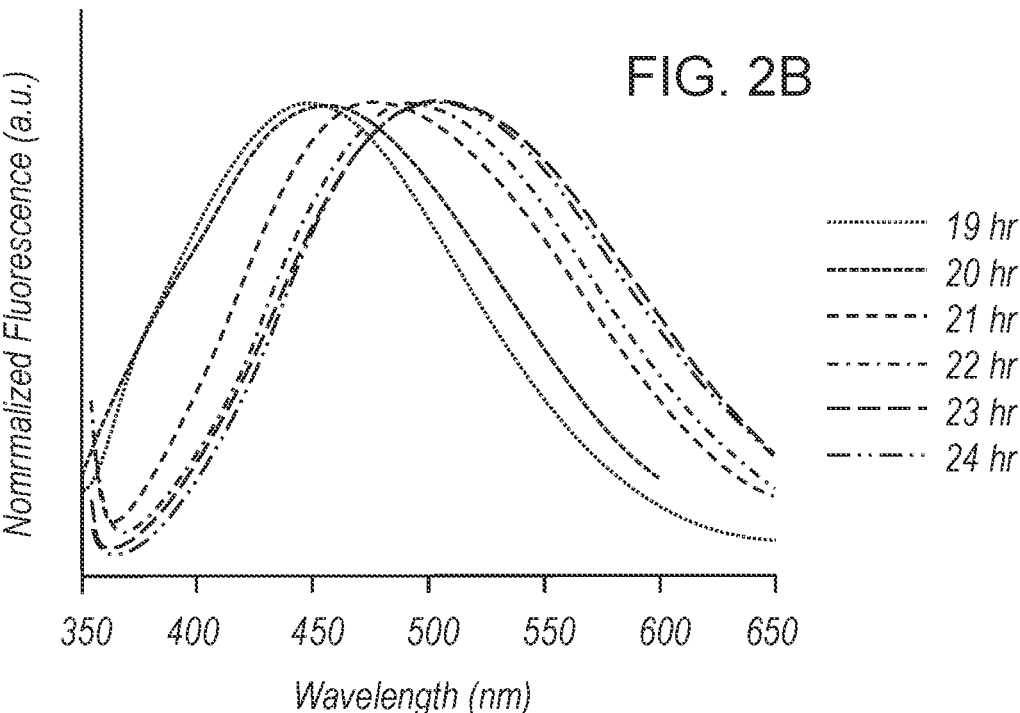

| Calculated FWGM values for the fluorescence spectra in FIG. 2B. | |
| --- | --- |
| Growth Time (hours) | FWHM (nm) |
| 19 | 156 |
| 20 | 170 |
| 21 | 169 |
| 22 | 163 |
| 23 | 177 |
| 24 | 171 |

Figure 3:
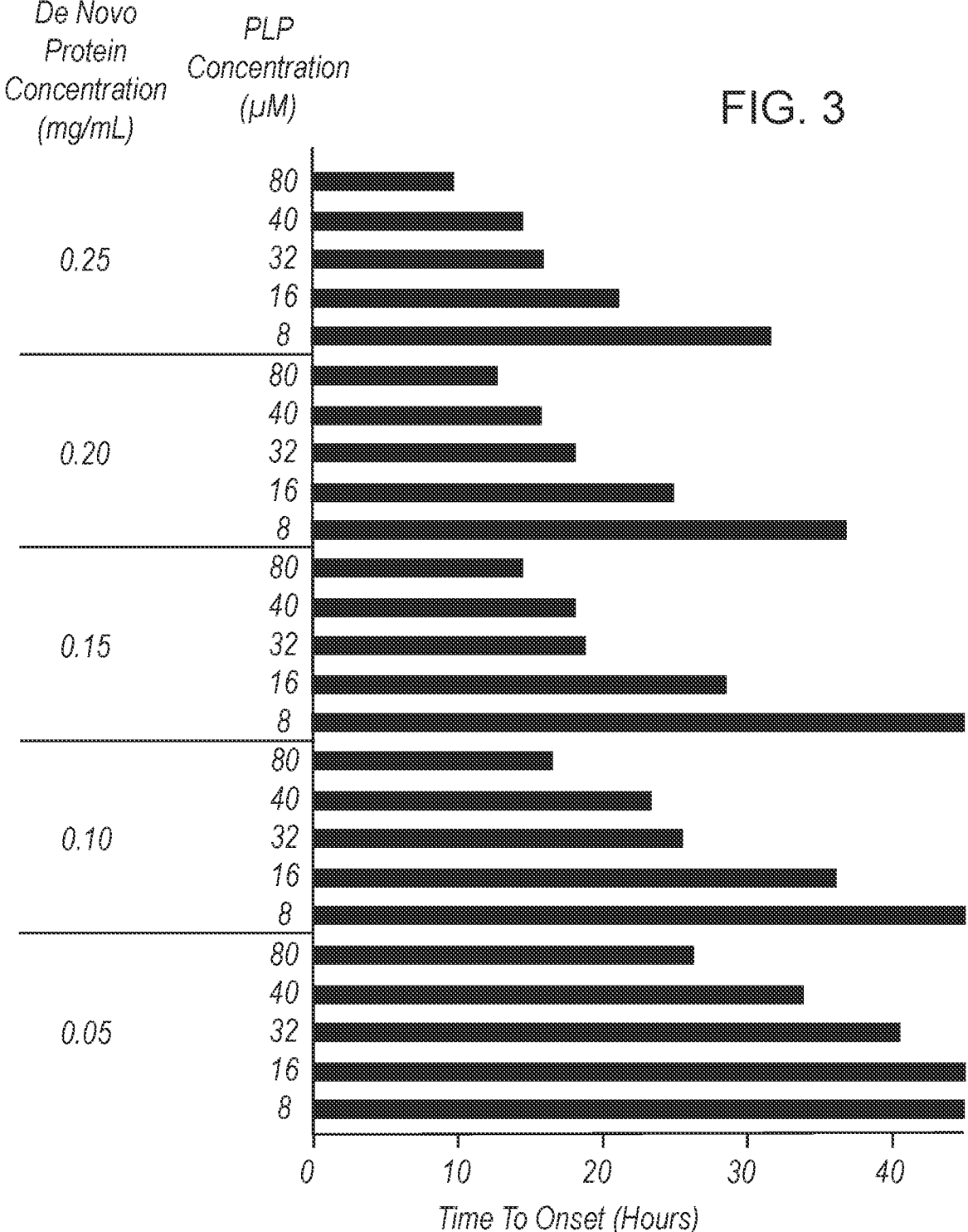
FIG. 3 is a graph showing the required time for the onset of CdS nanocrystal formation based on the concentrations of a de novo protein and PLP.

Not surprisingly, the time required to reach the onset of CdS nanocrystal formation depended on the concentration of ConK and PLP. See FIG. 3. When higher concentrations of ConK (0.25 mg/mL) and PLP (80 μM) were used, the appearance of a peak at 340 nm occurred after only 10 h. For low concentrations of PLP and ConK (e.g., combinations of 8 to 16 mM PLP and 0.05 to 0.1 mg/mL ConK), the onset of CdS quantum dots was not observed during the experimental time frame of 48 h. The long dwell time required for the formation of quantum dots suggests a slow generation rate of $H_2S$ by ConK, which is not surprising for a de novo protein that was not explicitly designed for this function.

The crystal morphology and nanocrystal size distribution were verified using XRD and TEM measurements. Importantly, semiconductor nanocrystals synthesized using the disclosed de novo proteins demonstrate improved stability compared to those obtained using naturally derived biomineralization pathways, making de novo biomineralization ideal for commercial implementation.

In some embodiments, the semiconductor may include a single crystal phase. This is a major difference between CdS quantum dots grown using the de novo proteins versus natural systems such as cystathionine γ-lyase (CSE). A mixed distribution of crystal phases is commonly observed for CdS nanocrystals synthesized at room temperature via natural biomineralization routes. In contrast, for synthesis of, e.g., CdS using the de novo proteins, a single phase of CdS, zinc blende, was observed. The dominance of zinc blende CdS is striking and indicates that the slow growth using ConK favors more controlled crystallization. This suggests that ConK could produce higher-quality crystallites at room temperature than those previously achieved by natural proteins.

To study the active site of one particular de novo protein, ConK, in the absence of an experimentally determined structure, AlphaFold was used to predict the structure. Because ConK appears to oligomerize in solution, the structure was modeled as either a monomer or a dimer. In the AlphaFold prediction, Lys56 (believed to be the active site for ConK) occurs in a semiexposed pocket in the 2nd interhelical turn of the protein. Because of the location of this turn, this binding pocket is the same in both the monomeric and dimeric states. Three relevant proximally close amino acids, His43, His46, and Phe47, were also identified. Aromatic amino acids are often observed in PLP-binding sites because they stabilize the pyridine ring through π-stacking. Similarly, histidines have also been shown to stabilize the pyridine ring by forming an H-bond with nitrogen. The proximity of both Phe and His side chains is consistent with natural PLP-dependent enzyme active sites. It is noted that although the active site of ConK shares several features with the PLP-binding sites in CSE, such as forming a Schiff base with lysine and the presence of aromatic amino acids, the sequence and structure of the active site pocket are dramatically different. This is expected as ConK has no evolutionary ancestry and was isolated from a library of semirandom de novo sequences.

Figures 4, 5:
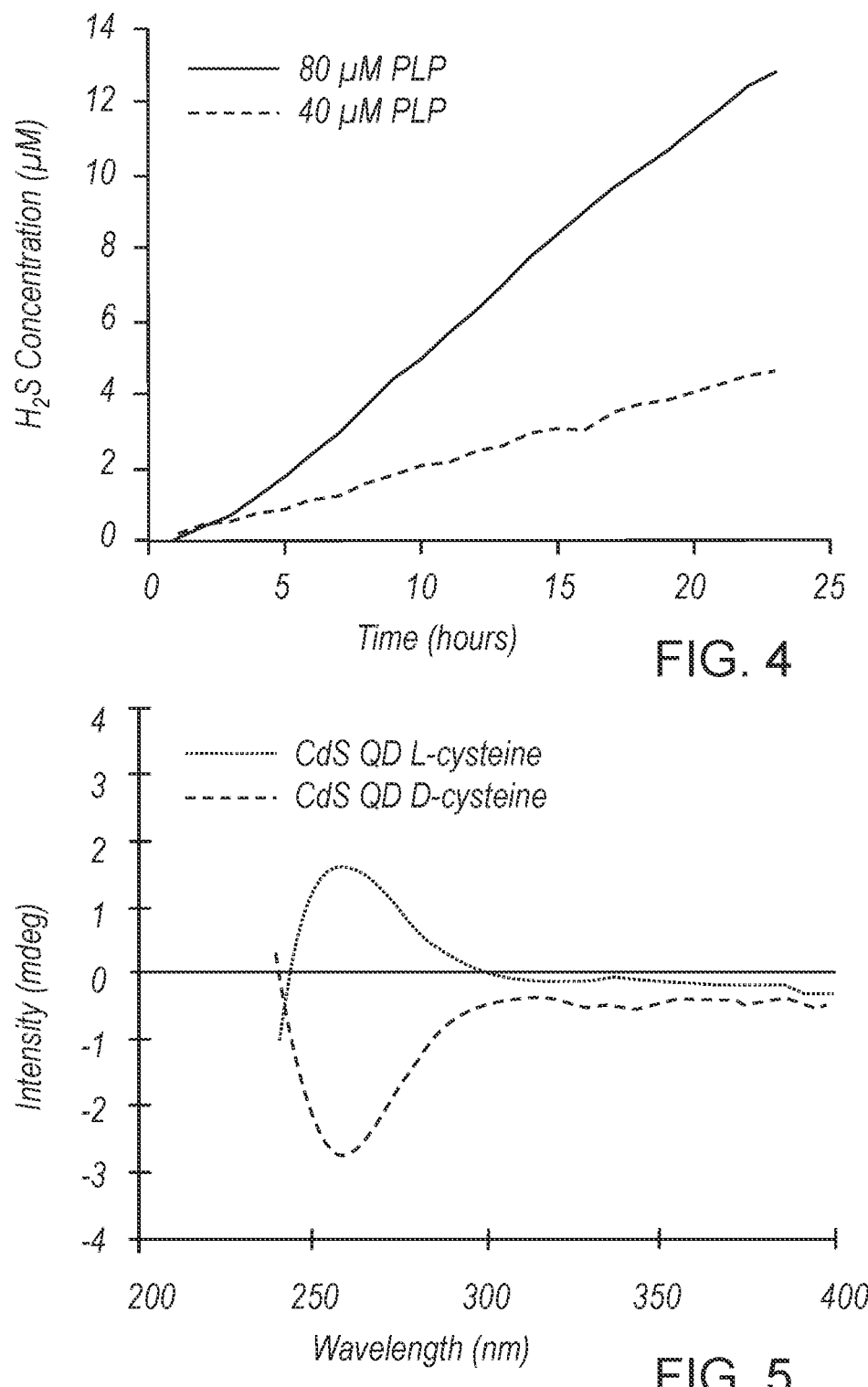
FIG. 4 is a graph showing average $H_2S$ generation over time for a solution containing 2.5 mM L-cysteine, 0.25 mg/mL ConK, and either 40 or 80 μM PLP.
FIG. 5 is a graph showing CD spectra of chiral CdS quantum dots synthesized using L- or D-cysteine; L-cysteine and D-cysteine alone give no signal in the excitonic region (>250 nm).

To assess the stereoselectivity of the ConK catalytic site, the L-cysteine was replaced with D-cysteine and the formation of CdS nanocrystals was monitored. Using D-cysteine led to an absorbance peak corresponding to CdS quantum dots, indicating that D-cysteine can also be turned over to $H_2S$ by ConK. Notably, cysteine plays a dual role in the system, acting as both a reactant and a capping ligand that stabilizes the quantum dot surface. It was found that the D-isomer can also serve as a capping agent. Following filtration using a 10-kDa MWCO filter to remove cysteamine adducts, the resulting CdS quantum dot solutions were assayed for chirality by CD spectroscopy. The signal was found to be exactly opposite when using D-cysteine (see FIG. 5), indicating that D-cysteine acts as a mirror image capping ligand on the surface of the CdS quantum dot.

The method may include one or more steps related to managing 65 the byproducts of the synthesis reaction. This may include capturing 70 $H_2S$ generated during the formation of the semiconductor nanocrystal (see, e.g., FIG. 4).

The captured $H_2S$ may then be utilize for various purposes. For example, in some embodiments, the method may include using 80 the captured $H_2S$ to synthesize a different material (such as a reduction of graphene oxide). Those of skill in the art will recognize the numerous reactions for which the captured $H_2S$ could be utilized.

In various aspects, a catalyzing agent may be provided. The catalyzing agent may include a de novo protein as disclosed herein, bound to a pyridoxal phosphate (PLP) cofactor. In some embodiments, the PLP will be bound to a lysine of the de novo protein. As discussed previously, preferably, the lysine will be within a binding pocket that is proximally close to at least one histidine and/or at least one phenylalanine when folded. The term "proximally close" as used herein refers to being sufficiently close to stabilize the pyridine ring of the PLP, e.g., via engaging in it-stacking or forming an H-bond with nitrogen.

In various aspects, a system may be provided. The system may include a buffer solution containing a metal salt, a sulfur-containing substrate in the buffer solution, and a de novo protein as disclosed herein in the buffer solution. In some embodiments, the system may also include PLP.

Various modifications may be made to the systems, methods, apparatus, mechanisms, techniques and portions thereof described herein with respect to the various figures, such modifications being contemplated as being within the scope of the invention. For example, while a specific order of steps or arrangement of functional elements is presented in the various embodiments described herein, various other orders/arrangements of steps or functional elements may be utilized within the context of the various embodiments. Further, while modifications to embodiments may be discussed individually, various embodiments may use multiple modifications contemporaneously or in sequence, compound modifications and the like.

Although various embodiments which incorporate the teachings of the present invention have been shown and described in detail herein, those skilled in the art can readily devise many other varied embodiments that still incorporate these teachings. Thus, while the foregoing is directed to various embodiments of the present invention, other and further embodiments of the invention may be devised without departing from the basic scope thereof. As such, the appropriate scope of the invention is to be determined according to the claims.

---

---

What is claimed:

1. A method for producing a semiconductor nanocrystal, comprising:
   adding a de novo protein, a metal salt, a sulfur-containing substrate, and a pyridoxal phosphate (PLP) to a buffer; and
   allowing a semiconductor nanocrystal to form;
   wherein the de novo protein comprises an amino acid sequence matching a binary pattern of polar (P) and nonpolar (N) amino acids, wherein the de novo protein is a PLP binding de novo Protein.

2. The method according to claim 1, wherein the de novo protein comprises an amino acid sequence having a sequence having at least 80% sequence identity to

[SEQ ID NO. 1]
MYGKLNEILE QFDEVLDQLD KNWHKRGNNL HDIEDELHQL

VKHFHHFMQG HKNEGKLQDM FDQMQQLLEN FDNHLQKRNE

TVHHIHEKLN QLIHQFDHLV HR.

3. The method according to claim 1, wherein the sulfur-containing substrate is an amino acid.

4. The method according to claim 3, wherein the amino acid is L-cysteine.

5. The method according to claim 3, wherein the amino acid is D-cysteine.

6. The method according to claim 1, wherein allowing the semiconductor nanocrystal to form comprises allowing the de novo protein to bind to the PLP to generate catalytic activity, and using the catalytic activity to produce the semiconductor nanocrystal.

7. The method according to claim 1, further comprising producing the de novo protein.

8. The method according to claim 7, further comprising purifying the de novo protein.

9. The method according to claim 1, further comprising allowing the formed semiconductor nanocrystal to grow to a predetermined size.

10. The method according to claim 1, wherein the semiconductor nanocrystal comprises a metal chalcogenide semiconductor nanocrystal.

11. The method according to claim 10, wherein the metal chalcogenide semiconductor nanocrystal is a CdS nanocrystal.

12. The method according to claim 1, wherein the metal salt comprises Cd.

13. The method according to claim 1, further comprising capturing $H_2S$ generated during formation of the semiconductor nanocrystal.

14. The method according to claim 13, further comprising using the captured $H_2S$ to synthesize a different material.

15. The method according to claim 14, wherein the synthesizing of a different material is a reduction of graphene oxide.

16. The method according to claim 1, wherein the semiconductor comprises a single crystal phase.

* * * * *